US00PP35514P2

(12) United States Plant Patent
Carter

(10) Patent No.: US PP35,514 P2
(45) Date of Patent: Nov. 28, 2023

(54) ***SALVIA* PLANT NAMED 'IGNITION CRANBERRY'**

(50) Latin Name: ***Salvia* x *jamensis***
Varietal Denomination: Ignition Cranberry

(71) Applicant: Kermit E. Carter, Elk, CA (US)

(72) Inventor: Kermit E. Carter, Elk, CA (US)

( * ) Notice: Subject to any disclaimer, the term of this patent is extended or adjusted under 35 U.S.C. 154(b) by 0 days.

(21) Appl. No.: 18/114,985

(22) Filed: Feb. 27, 2023

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./263.1, 475
See application file for complete search history.

*Primary Examiner* — Karen M Redden
(74) *Attorney, Agent, or Firm* — Weatherly IP Solutions, LLC; James M. Weatherly

(57) ABSTRACT

A new cultivar of *Salvia* named 'Ignition Cranberry' that is distinguishable by compact, low-growing plant habit and saturated blood red colored flowers.

2 Drawing Sheets

Genus and species: *Salvia* x *jamensis*.
Variety denomination: 'Ignition Cranberry'.

BACKGROUND

The present disclosure relates to a new and distinct cultivar of *Salvia* plant, also known as a sage, a perennial that is grown for use as an ornamental landscape and container plant. The new variety is known botanically as *Salvia* x *jamensis* and will be referred to hereinafter by the cultivar name 'Ignition Cranberry'.

'Ignition Cranberry' originated and was selected from a population of hybrid seedlings from a *Salvia* breeding program, which was started in 2010. The breeding program was conducted in the inventor's greenhouse nursery in Elk, Calif. The aim of the breeding program is to develop a uniform series of compact free-flowering varieties of *Salvia* x *jamensis* each with similar plant habits and flowering characteristics but with distinctly different flower colors. 'Ignition Cranberry' was selected by the inventor in 2019 from seedlings which resulted from the controlled hybridization using pollen collected from assembled selections from the inventor's large collection of *Salvia* varieties. The inventor applied the collected pollen to a selected unnamed female parent which bore red flowers. Seed from the female parent was grown out, and one seedling, which was named 'Ignition Cranberry', was selected for its saturated blood red colored flowers which were borne on compact low-growing plants with mid-green glossy leaves.

'Ignition Cranberry' was first asexually propagated in 2020 in a greenhouse at the inventor's nursery in Elk, Calif. using softwood tip cuttings. The inventor has confirmed that 'Ignition Cranberry' is stable and reproduces true to type in successive generations of asexual reproduction.

SUMMARY

The following traits have been repeatedly observed and represent the distinguishing characteristics of 'Ignition Cranberry'. 'Ignition Cranberry' has not been tested under all possible conditions and phenotypic differences may be observed with variations in environmental, climatic, and cultural conditions, without however, any variance in genotype.

1. 'Ignition Cranberry' exhibits a compact low-growing well-branched plant habit.
2. The flowers of 'Ignition Cranberry' are saturated blood red in color.
3. 'Ignition Cranberry' grows and flowers rapidly. Flowering plants may be produced in 10 to 12 weeks from a cutting.

DESCRIPTION OF THE PHOTOGRAPHS

The accompanying color photographs illustrate the overall appearance of the new *Salvia* cultivar 'Ignition Cranberry' showing the colors as true as it is reasonably possible to obtain in colored reproductions of this type. Photographs were taken in March 2022 in Santa Barbara, Calif. from a one-year-old plant grown outdoors in a 3.7-gallon (14 liter) container, with one pinch after initial cutting establishment and without any chemical growth regulators. Colors in the photographs may differ from the color values cited in the detailed botanical description, which more accurately describes the actual colors of the new variety 'Ignition Cranberry'.

DESCRIPTION OF THE NEW VARIETY

Figure 1:
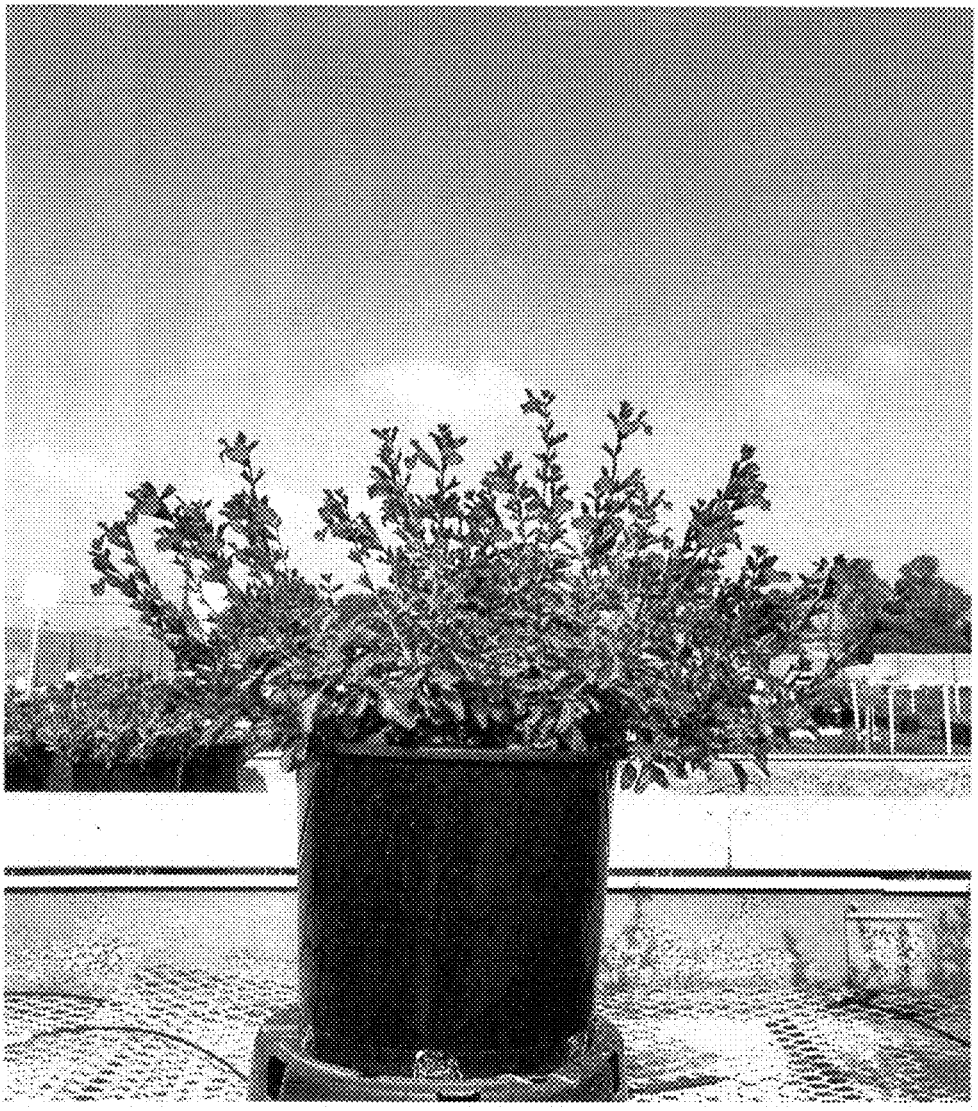
FIG. 1 depicts an entire plant in flower of 'Ignition Cranberry'.
Figure 2:
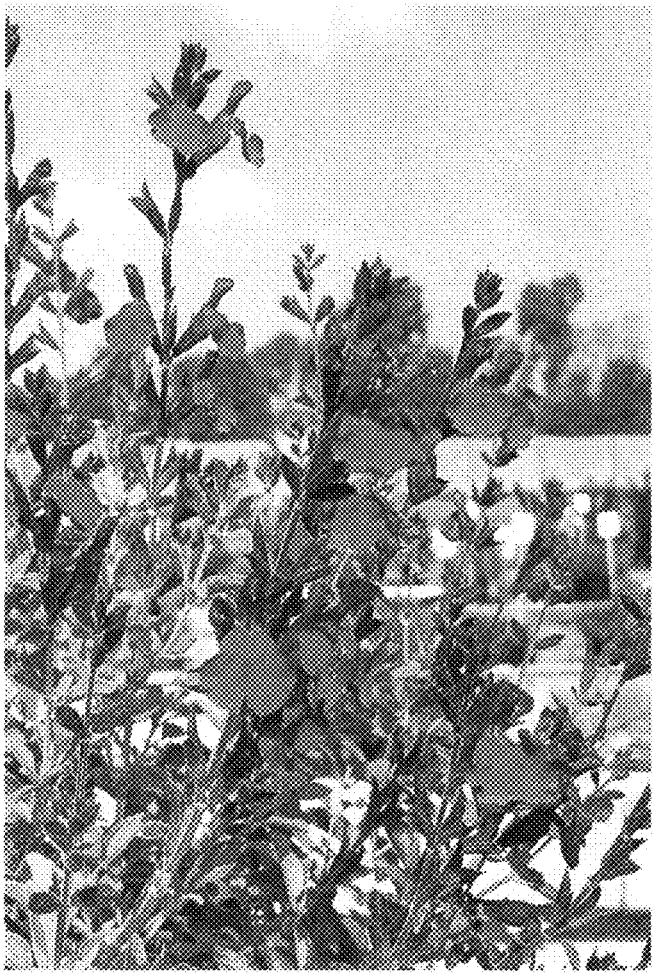
FIG. 2 depicts a close-up view of the inflorescences of 'Ignition Cranberry' showing the flowers and the terminal bud cluster.

The following detailed descriptions set forth the distinctive characteristics of 'Ignition Cranberry'. Observations, measurements, values, and comparisons were collected in March 2022 in Santa Barbara, Calif. from a one year old plant which had been growing outdoors in full sun in a 3.7 gallon (14 liter) container in Santa Barbara, Calif., with one pinch after initial cutting establishment and without any chemical growth regulators. Color determinations were made in accordance with The 2007 Royal Horticultural Society Colour Chart from London England, except where general color terms of ordinary dictionary significance are used.

Classification:

*Family*.—Lamiaceae.

*Genus*.—*Salvia*.

*Species*.—x *jamensis*.

*Common name*.—Sage.

Parentage:

*Female parent*.—Unnamed plant.

*Male parent*.—Unknown pollen donor varieties.

Plant:

*Propagation method*.—Softwood tip cuttings.

*Rooting system*.—Fine and fibrous.

*Vigor*.—Moderate vigor.

*Time to develop roots*.—5 days are needed for a cutting to develop roots at recommended rooting temperature of 20° to 22° Centigrade.

*Crop time*.—Approximately 12 weeks are required to produce a budded and flowering plant in a quart container. Larger containers require a longer period of growth in order to fill out. Flowering will continue throughout spring, summer and fall.

*Suggested container size*.—Quart to one-gallon container.

*Use*.—Ornamental for use as a landscape plant or container plant.

*Type*.—Perennial.

*Overall dimensions*.—After one year's growth in a 3.7 gallon container, 30 cm in height, including the inflorescence, and 50 cm in width.

*Cultural requirements*.—Grow in full sun with moderate water and well-draining soil.

*Hardiness*.—USDA Zone 7.

*Form*.—Low-growing bush.

*Growth habit*.—Compact.

*Blooming season*.—From one month after breaking spring dormancy to first frost.

*Lastingness of blooms*.—Inflorescence has some flower for 14 days, individual flowers last for 2 to 3 days.

Stems (below first pinch):

*Condition*.—Lignified.

*Bark*.—Papery, splitting.

*Shape*.—Round.

*Length*.—1 cm to 2 cm.

*Diameter*.—4 mm.

*Bark color*.—N200B.

*Stem color* (*where exposed beneath bark*).—143C.

*Shape*.—Square, edges rounded.

*Texture*.—Rough.

Branches:

*Quantity*.—Approximately 40, of which 6-8 are primary branches and 30 or more are secondary branches.

*Shape*.—Square, corners rounded.

*Length*.—11 cm to 13 cm measured to base of inflorescence.

*Width*.—3 mm at base, 2 mm at base of inflorescence.

*Internode length*.—Varies between 25 mm (primary branches), and 12 mm (secondary branches).

*Color*.—143C with prominent anthocyanin coloration on one or two faces of the lower internodes. Anthocyanin color, 187B.

Leaves:

*Type, arrangement*.—Simple, opposite.

*Attachment*.—Petiolate.

*Quantity per branch*.—6 to 8 pairs.

*Shape*.—Elliptic.

*Length*.—Up to 25 mm.

*Width*.—Up to 20 mm.

*Margin*.—Dentate, 12-15 teeth on each leaf side, teeth facing towards apex, depth 1.5 mm.

*Thickness*.—Moderately thick, slightly stiff.

*Venation*.—Pinnate, midrib slightly sulcate.

*Texture* (*both surfaces*).—Smooth, glabrous, matte.

*Color*.—Adaxial surface: 137A. Abaxial surface: N138C.

*Apex*.—Acute.

*Base*.—Cuneate.

*Fragrance*.—Pleasant sage fragrance when rubbed.

*Stipules*.—Present in one or two pairs at each leaf axil. Small, sessile, elliptic, up to 11 mm in length and 6 mm in width. Margins slightly dentate, color 137A (adaxial surface), N138C (abaxial surface), surfaces smooth, glabrous.

Petiole:

*Shape*.—Terete.

*Length*.—13 mm.

*Width*.—1.5 mm.

*Texture*.—Puberulent.

*Color*.—138B.

Peduncle:

*Length*.—18 mm.

*Shape*.—Square.

*Width*.—2 mm.

*Texture*.—Puberulent.

*Color*.—139C.

Inflorescence:

*Type*.—Terminal raceme. Flowers arranged in pairs, opposite, outward facing, rotated 30-40 degrees apart.

*Length*.—8 cm to 10 cm.

*Width*.—5 cm.

Pedicel:

*Length*.—6 mm.

*Diameter*.—1.0-1.5 mm.

*Texture*.—Puberulent.

*Color*.—N187B.

Calyx:

*Shape*.—Campanulate, flared toward the apex.

*Length*.—15 mm.

*Diameter at base*.—2 mm.

*Width*.—8 mm between sepal apices.

Sepals:

*Quantity*.—2, one upper, one lower, substantially longitudinally fused.

*Length*.—15 mm.

*Width*.—5 mm when flattened.

*Shape*.—Boat shaped.

*Apex*.—Acuminate.

*Base*.—Truncate.

*Margin*.—Entire.

*Texture*.—Adaxial surface: Puberulent, longitudinally ribbed. Ribs 1 mm apart, raised less than 0.1 mm. Abaxial surface: Glabrous, longitudinal depressions.

*Color*.—Adaxial surface: 187A. Abaxial surface: 194B, becoming N187B towards apex.

Flowers:

*Quantity.*—8 to 10 opposite pairs.

*Shape.*—Tubular, two-lipped.

*Fragrance.*—Pleasant sage fragrance.

Bud:

*Shape.*—Ellipsoidal on emergence from calyx, becoming cylindrical with rounded apex immediately prior to opening.

*Length.*—4 mm on emergence, 20 mm immediately prior to opening.

*Width.*—5 mm on emergence, 6 mm immediately prior to opening.

*Surface.*—Strongly pubescent, especially apex. Hairs dense, fine, 1 mm in length, color 71A.

*Color.*—71A.

Corolla:

*Shape.*—Tubular proximally to two-lipped distally, lower lip attitude relative to corolla is downward.

*Length.*—17 mm including corolla tube length 3 mm.

*Width.*—3 mm.

*Texture.*—Glossy, glandular.

*Color* (*both surfaces*).—71A, except tube base NN155D, translucent.

Petals:

*Quantity.*—2.

*Arrangement.*—One upper petal and one lower petal which appears as a large prominent lip with two lateral lobes fused to the lip and to each other.

*Upper petal.*—

*Shape.*—Hooded.

*Length.*—10 mm.

*Width.*—5 mm.

*Texture.*—Adaxial surface: Strongly pubescent. Hairs dense, fine, 1 mm in length, color 71A. Abaxial surface: Glabrous, with one longitudinal central rib.

*Apex.*—Rounded, with cluster of fine hairs approximately 1 mm in length, hair color 71A.

*Base.*—Truncate with lower lip at corolla mouth.

*Margin.*—Smooth, entire.

*Color.*—Adaxial surface: 71A. Abaxial surface: 70C, except central rib and margin 71A.

*Lower petal, lip.*—

*Shape.*—Broad cordate with deep apical notch.

*Length.*—10 mm from petal base to base of apical notch.

*Width.*—18 mm to 20 mm.

*Texture.*—Adaxial surface: Puberulent. Abaxial surface: Smooth, glabrous, semi-glossy.

*Apex.*—Emarginate, depth of notch 2 mm.

*Base.*—Truncate.

*Margin.*—Entire, gently undulating.

*Color.*—(both surfaces): 46A (deeply saturated).

*Lower petal, lateral lobes.*—

*Shape.*—Elliptic, fused at base, the pair appear as wings.

*Length.*—(each lateral lobe): 12 mm.

*Width.*—5 mm.

*Texture.*—Adaxial surface: Puberulent. Abaxial surface: Smooth, glabrous, semi-glossy.

*Apex.*—Rounded.

*Base.*—Truncate, tiny hairs clustered towards and at the base.

*Margin.*—Smooth, entire except for hairs at the base.

*Color* (*both surfaces*).—46A (deep, saturated).

Reproductive organs:

*Stamens.*—Quantity: 2. Length: 13 mm, each filament basally fused for 8 mm and free for 5 mm. Color: 70C.

*Anthers.*—Length: 1.5-2 mm. Width: 0.5 mm. Color: 165B.

*Pollen.*—Amount: Moderate. Color: 162C.

*Pistil.*—Quantity: 1. Stigma: Shape: Asymmetrically forked. Length: Longer fork 5 mm, strongly recurved; shorter fork 2 mm, gently recurved. Diameter 0.75 mm. Color: 70C, forks 71A. Style: Length (excluding stigma): 9 mm. Color: N155A towards base, becoming darker 70C towards stigma.

*Ovary* (*only observed unfertilized*).—Length: 3 mm. Width: 1.5 mm. Color: 150B.

Seed:

*Quantity, shape, dimensions.*—Sparse, ovoid, length 2.5 mm, diameter 1.25 mm. Color: Speckled, ranging between 165B and N199B. Surface: Smooth and matte.

Disease and pest susceptibility: Susceptible to aphids (*aphis gossypii*) when stressed. Generally outgrows most bacterial and viral infections. Resistant to deer and rabbit grazing.

Drought tolerance: Drought tolerant.

COMPARISON WITH PARENTAL LINES AND KNOWN VARIETY

In comparison with the assembled pollen donor varieties, 'Ignition Cranberry' exhibits a distinct combination of vigorous growth, profuse branching and saturated red flowers. None of the assembled pollen donor varieties, nor the selected female parent, exhibits the saturated blood red color of the flowers of 'Ignition Cranberry'.

'Ignition Cranberry' is closest in plant habit to the inventor's varieties *Salvia* 'Ignition Purple' (U.S. Plant Pat. No. 27,788) and *Salvia* 'Ignition Fuchsia' (U.S. Plant Pat. No. 32,046). The closest known variety of *Salvia* which bears similarly deep red flowers is *Salvia* X *greggii* 'Cherry Chief' (not patented). In comparison with 'Cherry Chief', whose mature height is between 60 and 90 cm, 'Ignition Purple' is more compact and low growing. In addition, the flowers of 'Cherry Chief' are less-saturated mid-red in color.

I claim:

1. A new and distinct cultivar of *Salvia* plant named 'Ignition Cranberry' as described and illustrated herein.

* * * * *